United States Patent [19]

Cianci et al.

[11] Patent Number: 4,692,150
[45] Date of Patent: Sep. 8, 1987

[54] TAMPER EVIDENT BAND

[75] Inventors: James P. Cianci, Gary; James R. Gross, St. Charles, both of Ill.

[73] Assignee: The Kendall Company, Boston, Mass.

[21] Appl. No.: 780,042

[22] Filed: Sep. 25, 1985

[51] Int. Cl.⁴ ............................................. A61M 5/00
[52] U.S. Cl. ................................. 604/111; 206/807; 604/905
[58] Field of Search ............... 604/111, 110, 160, 166; 206/807; 128/DIG. 18

[56] References Cited

U.S. PATENT DOCUMENTS

| | | | |
|---|---|---|---|
| 2,517,581 | 8/1950 | Lowry et al. | 128/DIG. 18 |
| 3,974,008 | 8/1976 | Choksi | 206/807 |
| 4,079,738 | 3/1978 | Dunn et al. | 604/165 |
| 4,194,509 | 3/1980 | Pickering et al. | 604/111 |
| 4,377,165 | 3/1983 | Luther et al. | 604/160 |
| 4,471,778 | 9/1984 | Toye | 604/160 |
| 4,475,903 | 10/1984 | Steenhuisen et al. | 128/DIG. 18 |

Primary Examiner—Stephen C. Pellegrino
Assistant Examiner—John D. Ferros
Attorney, Agent, or Firm—Donald N. Halgren

[57] ABSTRACT

A tamper-evident band for a liquid drainage system comprising an elastic catheter having an elongated shaft, a connector adjacent the proximal end of the catheter, and a drainage lumen extending through a major portion of the catheter and the connector. The tamper-evident band comprises elastomeric annular band of stepped diameter which is fit over the juncture between the connector and the proximal end of the catheter. The band has a slot longitudinally arranged on one outer peripheral portion of the band. It also has a semi-circumferential tear tab disposed on one end thereof. To separate the connector from the proximal end of the catheter, the band must be broken. The tab may be pulled and the band separated along its longitudinal slot. A small ring comprising the remaining stepped portion of the band remains on the adapter after the tab has been pulled, the slot fractured and the top band portion removed. This shows that there has probably been a band on the catheter and that the catheter has probably been separated from its connector.

13 Claims, 3 Drawing Figures

TAMPER EVIDENT BAND

BACKGROUND OF THE INVENTION

1. Field of the Invention

The present invention relates to catheter drainage systems, and more particularly to tamper bands placed on a catheter assembly.

2. Prior Art

Catheter drainage systems are utilized to drain urine from a patient's bladder. Such arrangements generally comprise a catheter having a distal end received in the patient's bladder and drainage lumen extending through the catheter, a hollow drainage tube and a collecting bag connected to a downstream end of the drainage tube, with an adapter at an upstream end of the drainage tube being received in a connector adjacent to the proximal end of the catheter. In use, urine drains from the bladder from the catheter and a drainage tube into the collection bag for collection therein. Such drainage systems are sterile and are closed to the atmosphere to prevent the bacteria from entering the system which might otherwise pass by retrograde movement into the bladder with possible deleterious results to the patient. In particular it is undesirable to remove the adapter from the catheter connector since such a procedure could allow entry of bacteria into the patient. Hence, it is desirable to discourage such disconnection, and at the very least, it is desirable to know when such a disconnection has taken place. A recent patent application Ser. No. 630,175 shows a means for discouraging tampering with a liquid drainage catheter system. The tamper discouraging device therein comprises a heat shrinkable band circumferentially arranged against the catheter over the connector and the adapter.

A further tamper discouraging system is shown in U.S. Pat. No. 4,194,509. This arrangement uses a piece of tape which is wrapped around the junction of the proximal end of the catheter and the adapter. The tape has heat applied to it so it will shrink about that juncture. An unfortunate characteristic of tape, is that it has sharp edges, which may rub a patient's thigh during use thereof and can be very uncomfortable. Have you ever seen a corner of a piece of tape that has not lifted up?.

It is an object of the present invention to provide a pre-connected drainage system with a catheter which is sealed to a drainage tube by a tamper-evident encircling means which means will not make the patient uncomfortable.

It is a further object of the present invention to define a tamper-evident means on a pre-connection arrangement whereby disconnection of the system is evident by a portion of that means remaining on the connector.

It is yet a further object of the present invention to provide a tamper-evident means which also displays information thereon.

BRIEF SUMMARY OF THE INVENTION

The present invention comprises a tamper-evident seal arrangement for affecting a positive interlock between a catheter and a drainage tube adapter in a catheter drainage system. The possibility of accidental disconnection is avoided, and any intentional disconnection of the system is evident from mere inspection thereof.

The seal arrangement of the present invention comprises an annular silicone band having two ring portions of stepped configuration. One band has a tab portion on one end thereof. A longitudinally directed tear or break-away seam is arranged across one ring portion of the band in axial alignment with one edge of the tab. The seal arrangement also has a thin circumferential web disposed therearound which comprises the tear strip thereon and which joins the two ring portions together. When the tab is pulled, one of the ring portions is permitted to be pulled off of the connector. Thus, an annular portion of band remains about the connector. The remaining band may be colored or have instructional indicia thereon. The tamper-evident seal is preferably placed on the catheter assembly during the initial manufacture of the drainage system. The seal arrangement is made from silicone and it is placed in a solvent bath such as Freon. The seal arrangement is thus temporarily caused to expand. The seal arrangement is then placed over the adapter at the junction of the connector and the drainage tube. The seal arrangement returns to its original size after a short interval of time. Thus, a soft conforming annular band is disposed about the juncture of the connector and the drainage tube, providing a soft resilient tamper-evident means which will not bother the patient against whom the catheter is taped.

BRIEF DESCRIPTION OF THE DRAWINGS

The objects and advantages of the present invention will become more apparent when viewed in conjunction with the following drawings in which.

DESCRIPTION OF THE PREFERRED EMBODIMENT

Figure 1:
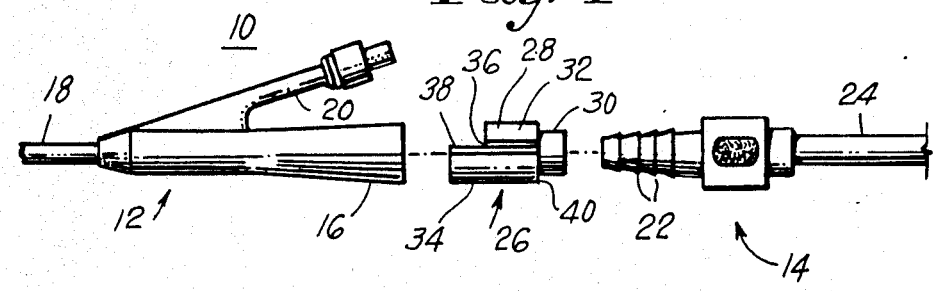
FIG. 1 is an exploded view of a catheter drain assembly having a tamper-evident system therewith.

Referring now to the drawings in detail, and particularly to FIG. 1, there is shown a portion of a catheter drainage assembly 10, in a "pre-connected" orientation. The catheter drainage assembly 10 comprises a Foley catheter 12 arrangeable with a drainage tube adapter 14 for mating in a telescopic arrangement with a funnel 16 at the proximal end of the catheter 12. The distal end of the catheter 12 comprises a flexible tubing 18 which may have one or more lumens, not shown, therein. The distal end of the flexible tubing 18 is that end which is inserted into a patient. The catheter 12 may have a side arm 20 which is in fluid communication with one of the lumens of the flexible tube 18. The side arm 20 is utilized to provide fluid to the distal end of the flexible tubing for purposes of inflating an inflatable balloon thereat. A second side arm, not shown, may be utilized for the distribution of medication or the like. The drainage tube adapter 14 may have a step-like configuration 22 on its distal end, which ultimately mates telescopically with the funnel 16 of the catheter 12. The proximal end of the drainage tube adapter 14 is attached to a drainage tube 24 which ultimately leads to the drainage or collection bag, not shown.

Figure 2:
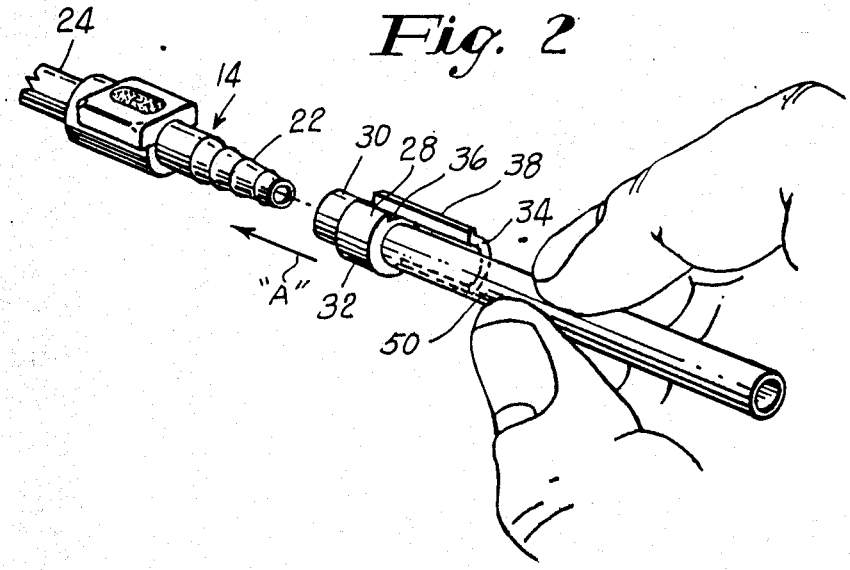
FIG. 2 is a perspective view of a portion of the catheter assembly.
Figure 3:
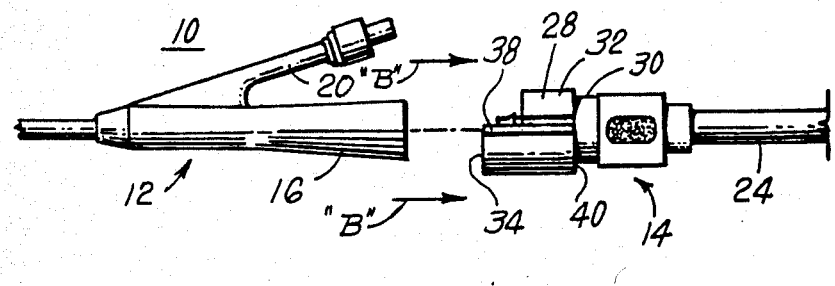
FIG. 3 is a side elevational view of a portion of the catheter assembly.

There is shown in FIG. 1, a tamper-evident means 26, comprising a resilient band 28 of stepped configuration. The band 28 has a proximal portion 30 of narrow diameter tearably attached to a distal band portion 32 of slightly larger diameter than on the distal end thereof. The larger band portion 32 has a tab 34 on its distal edge, of semi-circumferential configuration. A slot 36 is disposed on the larger diameter band which is in axial alignment with an axially disposed edge 38 of the tab 34. The slot 36 is comprised of a radially thinner seam of band material. A thin membrane 40 made of silicone rubber is also disposed between the larger band portion 32 and the smaller band portion 30. The thin membrane 40 holds the two different sizes of bands 30 and 32 together. The slot 36 and the membrane 40 are each tearable. The band 28, may preferably be made of an expandable material such as silicone rubber, and may be immersed for about 20 to 30 minutes in a solvent bath such as freon, not shown, which causes it to enlarge. The band 28 is preferably made of silicone, which is expandable in fluronated hydrocarbons such as freon, or in chloronated hydrocarbons such as chloroform, carbon tetra chloride, dichloro methane or tetra chloro ethylene. The band 28 may also be made of polyurethane which is expandable in the above-recited chloronated hydrocarbons and alcohols such as ethanol, isopropanol or methanol. Once the band 28 has remained in the bath for a sufficient amount of time, a small applicator tube 50 may be disposed onto one end, the distal end of the band 28, as shown in FIG. 2. The still enlarged silicone band 28 may then be pushed over the distal end of the drainage tube adapter 14 in the direction as shown by the arrow "A" in FIG. 2, or the assembly operation may be done entirely manually. The funnel 16 of the Foley catheter 12 may then be inserted into the distal end of the band 28, as shown by the arrows marked "B" in FIG. 3. The tab 34 portion of the band is disposed radially outwardly of the funnel 16. After a short period of time the band 28 begins to return to its normal diameter which is just slightly less than the outside diameter of the distal end of the drainage tube adapter 14 and the funnel 16. When it is necessary to remove the catheter from the drainage tube 14 either for irrigation or for cleaning thereof, the tab 34 may be pulled radially outwardly so as to fracture the elongated slot 36 that is axially disposed on the side of the larger diameter band 32. The thin web or membrane 40 which secures the larger band 32 to the smaller band 30 is also fractured so as to separate the larger band 32 from the smaller band 30. The smaller band 30 is thus retained annularly around the periphery of the drainage tube adapter 14, thus showing that there had been a joining of the catheter 12 therewith which may have been displaced permitting whatever precautions to then be taken. The smaller band 30 may be of a bright color so as to be noticed easily, or it may have printing or other instructional indicia thereon.

Thus has been shown an apparatus and method of incapsulating the junction of the funnel 16 of a catheter 12 with a drain port of a drainage tube adapter 14. The tamper-evident band 28 also protects the junction from intimate contact with bacteria, thereby providing the sterial barrier while it is in place. The automatic returning of the band 28 to its original diameter after its "bath" from its enlarged diameter also reinforces the junction between the catheter 12 and the drainage tube adapter 14.

I claim:
1. A catheter drainage assembly comprising:
   a catheter having a funnel at its proximal end;
   a drainage tube adapter matable with said funnel; and
   a tamper-evident band means comprising a tearable solvent expandable annular ring disposed about the juncture of said funnel and said drainage tube adapter.
2. A catheter drainage assembly as recited in claim 1, wherein said band has a slot of diminished thickness of material to facilitate tearing thereof.
3. A catheter drainage assembly as recited in claim 1, wherein said band is comprised of two generally annular portions attached by a tearable web of material therebetween.
4. A catheter drainage assembly, as recited in claim 1, wherein said band has a semi-circumferentially arranged tab disposed off of the edge of one end of said band.
5. A catheter drainage assembly as recited in claim 1, wherein said band is resilient and soft so as to minimize abrasive discomfort to a patient against whom it is attached.
6. A catheter drainage assembly as recited in claim 3 wherein the outer diameter of each of said annular portions is different.
7. A catheter drainage assembly as recited in claim 1, wherein said band is selected from the group of materials comprising silicone or polyurethane.
8. A catheter drainage assembly as recited in claim 1, wherein said expandable band expands when bathed in fluronated or chloronated hydrocarbon solvents selected from the group consisting of freon, chloroform, dichloromethane, or tetrachloromethane.
9. A method of assembling a tamper-evident band onto a catheter drainage assembly comprising the steps of:
   providing a catheter having a proximal end;
   providing a drainage tube having a distal end matable with the proximal end of said catheter; and
   providing a solvent expandable annular band which is disposable while expanded, about the juncture of the drainage tube and the catheter.
10. A method of assembly, as recited in claim 9, including the step of:
    bathing the annular band in a solvent so as to cause said band to expand.
11. A method of assembly as recited in claim 10, including the step of:
    placing the expanded band on either the distal end of the drainage tube.
12. A method of assembly as recited in claim 11, including the step of:
    mating the drainage tube and the catheter with the band disposed around the juncture thereof.
13. A method of assembly as recited in claim 12, including the step of:
    returning the band to its original diameter so as to fit snugly around said juncture of said drainage tube and said catheter.

* * * * *